US006077541A

United States Patent [19]
Chen et al.

[11] Patent Number: 6,077,541
[45] Date of Patent: *Jun. 20, 2000

[54] OMEPRAZOLE FORMULATION

[75] Inventors: Chih-Ming Chen, Davie; Joseph C. H. Chou, Coral Springs; Timothy Weng, Plantation, all of Fla.

[73] Assignee: Andrx Pharmaceuticals, Inc., Fort Lauderdale, Fla.

[ * ] Notice: This patent is subject to a terminal disclaimer.

[21] Appl. No.: 09/335,575

[22] Filed: Jun. 18, 1999

Related U.S. Application Data

[62] Division of application No. 08/970,489, Nov. 14, 1997.

[51] Int. Cl.$^7$ ...................................................... A61K 9/34
[52] U.S. Cl. .......................... 424/480; 424/479; 424/475; 424/474
[58] Field of Search ..................................... 424/474, 475, 424/476, 477, 479, 480, 481, 482

[56] References Cited

U.S. PATENT DOCUMENTS

| | | |
|---|---|---|
| 4,045,563 | 8/1977 | Berntsson et al. . |
| 4,045,564 | 8/1977 | Berntsson et al. . |
| 4,182,766 | 1/1980 | Krassó et al. . |
| 4,255,431 | 3/1981 | Junggren et al. . |
| 4,337,257 | 6/1982 | Junggren et al. . |
| 4,359,465 | 11/1982 | Ruwart . |
| 4,432,966 | 2/1984 | Zeitoun et al. . |
| 4,508,905 | 4/1985 | Junggren et al. . |
| 4,544,750 | 10/1985 | Brändström et al. . |
| 4,620,008 | 10/1986 | Brändström et al. . |
| 4,636,499 | 1/1987 | Brändström et al. . |
| 4,686,230 | 8/1987 | Rainer et al. ............................ 514/338 |

(List continued on next page.)

FOREIGN PATENT DOCUMENTS

| | | |
|---|---|---|
| 1127158 | 7/1982 | Canada . |
| 1129417 | 8/1982 | Canada . |
| 1234118 | 3/1988 | Canada . |
| 1263119 | 11/1989 | Canada . |
| 1264751 | 1/1990 | Canada . |
| 1292693 | 12/1991 | Canada . |
| 2083605 | 12/1991 | Canada . |
| 1302891 | 6/1992 | Canada . |
| 2046364 | 1/1993 | Canada . |
| 1324758 | 11/1993 | Canada . |
| 2140347 | 2/1994 | Canada . |
| 2170250 | 1/1995 | Canada . |
| 2166483 | 5/1995 | Canada . |
| 2170647 | 1/1996 | Canada . |
| 2193681 | 1/1996 | Canada . |
| 1338377 | 6/1996 | Canada . |
| 2037101 | 3/1997 | Canada . |
| 2166794 | 3/1997 | Canada . |
| 0124495 | 8/1984 | European Pat. Off. . |
| 0173664 | 9/1985 | European Pat. Off. . |
| 1234058 | 6/1971 | United Kingdom . |
| WO8503436 | 8/1985 | WIPO . |
| 9402140 | 8/1993 | WIPO . |
| WO9501783 | 1/1995 | WIPO . |

(List continued on next page.)

OTHER PUBLICATIONS

L. Olbe, S.E. et al., Present Situation and Future Prospects of Medical Treatment., Gastrins and the Vagus, Academic Press p. 245–250, 1979.

M.R. Thompson, The Unnatural History of Drug–Associated Gastric Ulcers., Gut, vol. 22, No. 10, Oct. 1981.

Eric Fellenius et al., Substituted Benzimidazoles Inhibit Gastric Acid Secretion by Blocking (H+ + K+) ATPase., Nature, vol. 290, Mar. 12, 1981.

Tore Lind, et al., Effect of Omeprazole—A Gastric Proton Pump Inhibitor on Pentagastrin Stimulated Acid Secretion in Man., Gut, vol. 24 p. 270–276, 1983.

K–Fr Sewin et al., Effect of Substituted Benzimidazoles on Acid Secretion in Isolated and Enriched Guinea Pig Parietal Cells., Gut, vol. 24 p. 557–560, Jun. 1983.

Haken Larsson et al., Inhibition of Gastric Acid Secretion by Omeprazole in the Dog and the Rat., Gastroenterology, vol. 85 p. 900–907, Oct. 1983.

Walter London et al., Dose–Response Study of Omeprazole on Meal Stimulated Gastric Acid Secretion and Gastrin Release., Gastroenterology, vol. 85 p. 1373–1378, Dec. 1983.

Stanislaw J., Effects of Omeprazole, a Substituted Benzimidazole, on Gastrointestinal Secretions, Serum Gastrin and Gastric Mucosal Blood Flow on Dogs., Gastroenterology, vol. 86, p. 71–77, Jan. 1984.

D.A. Henry et al., Omeprazole: Effects on Oxidative Drug Metabolism., British Journal of Clinical Pharmocology, vol. 18, p. 195–200, Aug. 1984.

B.K. Sharma et al. Optimal Dose of Omeprazole for Maximal 24 Hour Decrease of Intragastric Acidity. Gut, vol. 25 p. 957–964, Sep. 1984.

H.P.M. Festen et al., Effect of Oral Omeprazole on Serum Gastrin and Serum Pepsinogen I Levels. Gastroenterolgy, vol. 87 p. 1030–1034, Nov. 1984.

Peter Prichard et al., Omeprazole: A study of its Inhibition of Gastric pH and Oral Pharmacokinetics After Morning or Evening Dosages, Gastroenterology, vol. 88, Jan. 1985.

K.O. Borg and L. Olbe, Omeprazole—A Study fo Preclinical Data, Gastroenterology, p. 15–22, 37–51, 71–77, 79–93, 105–120, Jun. 1985.

50th Ed. Physician's Desk Reference p. 529–531.

K.O. Borg, L. Olbe Proceedings of the First International Symposium on Omeprazole, Supplement to the Scandinavian Journal of Gastroenterology, pp. 11–17, 31–38, 54–56, 59–60, 75–76, 77–78, 89–91, 92–98, 99–104, 105–135, 179, 182–183, 187–195, 1996.

*Primary Examiner*—Michael A. Williamson
*Attorney, Agent, or Firm*—Biedman, Gibson & Costigan, P.C.

[57] ABSTRACT

A pharmaceutical composition of omeprazole for oral administration is described which consists essentially of:
(a) a pellet comprising an inert core component, a therapeutically effective amount of omeprazole, a surface active agent, a filler, a pharmaceutically acceptable alkaline agent and a binder; and
(b) a single layer of coating on said pellet which comprises a layer of an enteric coating agent.

14 Claims, No Drawings

U.S. PATENT DOCUMENTS

| | | |
|---|---|---|
| 4,738,974 | 4/1988 | Brändström . |
| 4,786,505 | 11/1988 | Lovgren et al. . |
| 4,840,799 | 6/1989 | Appeigren et al. . |
| 4,853,230 | 8/1989 | Lovgren et al. . |
| 5,045,321 | 9/1991 | Makino et al. . |
| 5,093,132 | 3/1992 | Makino et al. . |
| 5,093,342 | 3/1992 | Tomoi et al. . |
| 5,178,867 | 1/1993 | Guittard et al. . |
| 5,204,118 | 4/1993 | Goldman et al. . |
| 5,219,870 | 6/1993 | Kim . |
| 5,232,706 | 8/1993 | Polomo Coll . |
| 5,244,670 | 9/1993 | Upson et al. . |
| 5,288,506 | 2/1994 | Spickett et al. . |
| 5,304,540 | 4/1994 | Blackburn et al. . |
| 5,330,982 | 7/1994 | Tyers . |
| 5,352,688 | 10/1994 | Kaminski . |
| 5,362,424 | 11/1994 | Lee et al. . |
| 5,385,739 | 1/1995 | Debregeas et al. . |
| 5,389,664 | 2/1995 | Baile et al. . |
| 5,399,700 | 3/1995 | Min et al. . |
| 5,417,980 | 5/1995 | Goldman et al. . |
| 5,433,959 | 7/1995 | Makino et al. . |
| 5,508,041 | 4/1996 | Lee et al. . |
| 5,518,730 | 5/1996 | Fuisz . |
| 5,599,794 | 2/1997 | Eek et al. . |
| 5,620,964 | 4/1997 | Roth et al. . |
| 5,622,717 | 4/1997 | Fuisz . |
| 5,637,320 | 6/1997 | Bourke et al. . |
| 5,639,478 | 6/1997 | Makino et al. . |
| 5,693,818 | 12/1997 | Von Unge . |
| 5,714,504 | 2/1998 | Lindberg et al. . |
| 5,753,265 | 5/1998 | Bergstrand et al. ................... 424/474 |

FOREIGN PATENT DOCUMENTS

| | | |
|---|---|---|
| WO9510264 | 4/1995 | WIPO . |
| WO9601622 | 1/1996 | WIPO . |
| WO9601623 | 1/1996 | WIPO . |
| WO9602535 | 2/1996 | WIPO . |
| 9624338 | 8/1996 | WIPO . |
| WO9624375 | 8/1996 | WIPO . |
| WO9601612 | 1/1999 | WIPO . |
| 9906032 | 2/1999 | WIPO . |

OMEPRAZOLE FORMULATION

This is a divisional application of U.S. patent application Ser. No. 08/970,489 that was filed on Nov. 14, 1997.

BACKGROUND OF THE INVENTION

The present invention relates to a stable formulation of omeprazole. It is well known that omeprazole is sensitive to acidic conditions and the after contact with an acid, omeprazole will degrade and will not function in its intended manner. Initially, alkaline materials were added to a core of omeprazole and later an enteric coating was applied over the core to prevent the omeprazole from contacting the acidic pH conditions of the stomach. This approach is satisfactory if the product is administered within a short time after it is manufactured but if the product is stored under ambient conditions, the acidic residue of the enteric coating appears to degrade the omeprazole before it is administered to a patient. To solve this problem, the prior art has used a separate layer of a coating agent to coat a pellet core which contains omeprazole and an alkaline material which is thereafter coated with the enteric coating. This technique is described in U.S. Pat. No. 4,786,505.

This dual layer coating technique requires the application of two separate functional coating operations which increases the length of the manufacturing process and the cost of the product. The applicants have surprisingly discovered a coating system which avoids the need to use a coating layer to separate the omeprazole core from the enteric coating layer in an omeprazole dosage form. The separate coating system is based on the combined use of an enteric coating agent which is applied to pellet cores of omeprazole as a suspension in an suitable solvent.

SUMMARY OF THE INVENTION

The present invention provides a novel dosage form of omeprazole which consists essentially of:

(a) a pellet comprising an inert core component, a therapeutically effective amount of omeprazole, a surface active agent, a filler, a pharmaceutically acceptable alkaline agent and a binder; and (b) a single layer of coating on said pellet which comprises a layer of an enteric coating agent.

Accordingly, it is a primary object of this invention to provide a pharmaceutical dosage formulation of omeprazole which is stable upon prolonged storage, is stable when administered to a patient and is capable of providing the desired therapeutic effect.

It is also an object of this invention to provide a pharmaceutical dosage form of omeprazole which is bioequivalent to dosage forms of omeprazole which have an intermediate layer of an inert coating material.

It is also an object of this invention to provide a stable dosage form of omeprazole which may be produced without the need to provide an intermediate coating layer that separates the omeprazole containing core from the enteric coating layer.

These and other objects of the invention will become apparent from a review of the appended specification.

DETAILED DESCRIPTION OF THE INVENTION

The omeprazole formulation of the invention is preferably based on pellets having a core forming inert component which may comprise a starch or sugar sphere such as non-pareil sugar seeds having an average size of from 14 to 35 mesh, preferably about 18 to 20 mesh. The core forming inert component is coated with a formulation which comprises omeprazole, a surface active agent, a filler, an alkaline material and a binder, which are collectively referred to hereafter as the drug layer composition. The core forming inert component is employed at 1:1 to 5:1 and preferably from 2:1 to 3:1 weight ratio to the drug layer composition.

The omeprazole may comprise from 20 to 70 wt % and preferably 40 to 50 wt % of the drug layer composition.

The surface active agent may be any pharmaceutically acceptable, non-toxic surfactant. Suitable surface active agents include sodium lauryl sulfate, polysorbate 20, polysorbate 40, polysorbate 60, polysorbate 80 and the like.

The surface active agent may be present at a level of from 0.1 to 5 wt % and preferably 0.25 to 2.5 wt % based on the total weight of the drug layer composition.

The alkaline material is selected from the group consisting of the sodium, potassium, calcium, magnesium and aluminum salts of phosphoric acid, carbonic acid, citric acid and aluminum/magnesium compounds such as $Al_2O_3 \cdot 6MgO \cdot CO_2 \cdot 12H_2O$, $(Mg_6Al_2(OH)_{1-6} \; CO_3 \cdot 4H_2O)$, $MgO \cdot Al_2O_3 \cdot 2SiO_2 \cdot nH_2O$ where n is a whole integer of 2 or more. In addition the alkaline material may be selected from the group consisting of antacid materials such as aluminum hydroxides, calcium hydroxides, magnesium hydroxides and magnesium oxide. The alkaline agent may be present at a level of 1 to 20 wt % based on the total weight of the coating composition, depending on the relative strength of the alkaline material. If the preferred disodium phosphate alkaline agent is employed, a level of from 1 to 10 wt % and preferably 4 to 7 wt % based on the weight of the drug layer composition may be employed.

The binder may be any pharmaceutically acceptable, non-toxic pharmaceutically acceptable binder.

The binder is preferably a water soluble polymer of the group consisting of polyvinyl alcohol, polyvinylpyrrolidone, methylcellulose, hydroxypropyl cellulose, hydroxymethyl cellulose and the like. A water soluble binder is preferred which is applied from an aqueous medium such as water at a level of from 0.1 to 5 wt % and preferably from 0.25 to 3 wt % of binder based on the total weight of the drug layer composition.

A filler is added to the drug layer. Sugars such as lactose, dextrose, sucrose, maltose, microcrystalline cellulose and the like may be used as fillers in the pellet coating composition. The filler may comprise from 20 to 70 wt % and preferably 40 to 50 wt % based on the total weight of the drug layer composition.

The enteric coating agent may comprise a acid resisting material which resists acid up to a pH of above about 5.0 or higher which is selected from the group consisting of cellulose acetate phthalate, hydroxypropylmethyl cellulose phthalate, polyvinyl acetate phthalate, carboxymethylethylcellulose, Eudragit L (poly(methacrylic acid, methylmethacrylate), 1:1 ratio; MW (No. Av. 135,000—USP Type A) or Eudragit S (poly(methacrylic acid, methylmethacrylate, 1:2 ratio MW (No. Av. 135,000—USP Type B) and mixtures thereof.

The enteric coating agent may also include an inert processing aid in an amount from 10 to 80 wt % and preferably 30 to 50 wt % based on the total weight of the acid resisting component and the inert processing aid. The inert processing aids include finely divided forms of talc, silicon dioxide, magnesium stearate etc. Typical solvents which may be used to apply the acid resisting component-inert processing aid mixture include isopropyl alcohol, acetone, methylene chloride and the like. Generally the acid resistant component-inert processing aid mixture will be applied from a 5 to 20 wt % of acid resisting component-inert processsing aid mixture based on the total weight of the solvent and the acid resistant component-inert processing aid.

The cores are formed by spraying the non-pareil seeds with an aqueous or non-aqueous suspension which contains the alkaline agent, the omeprazole, the surface active agent and the binder. The suspension medium may comprise any low viscosity solvent such as water, isopropyl alcohol, acetone, ethanol or the like. When fluids such as water are employed, this will usually require a weight of fluid which is about seven times the weight of the dry components of the coating composition.

After the cores are dried, the cores are coated with the enteric coating agent. A color imparting agent may be added to the enteric coating agent mixture or a rapidly dissolving seal coat containing color may be coated over the enteric coating agent layer provided that the seal coat is compatible with and does not affect the dissolution of the enteric coating layer.

DESCRIPTION OF THE PREFERRED EMBODIMENTS

EXAMPLE 1

Active pellets of omeprazole are formed by placing sugar spheres in a fluidized bed coater and spraying a suspension containing omeprazole onto the sugar spheres. The formulation for making the active pellets has the following composition:

| | |
|---|---|
| povidone, USP (Plasdone K90) | 4.5 g |
| sodium lauryl sulfate, NF | 10.6 g |
| lactose anhydrous, NF | 427.7 g |
| disodium phosphate, NF | 51.3 g |
| omeprazole, USP (micronized) | 427.7 g |
| purified water, USP | 3336.0 g |

The povidone, lactose anhydrous, disodium phosphate and the purified water are mixed with a mechanical mixer until the materials are dissolved. Then the sodium lauryl sulfate is added to the mixture with gentle stirring to avoid the formation of excess foam until it dissolves completely. At that time the micronized omeprazole is added to the mixture and gentle stirring is continued until the micronized omeprazole is completely dispersed.

2500.0 g of non-pareil sugar spheres (USPXII) (18/20 mesh) are placed in the fluidized bed coater and the suspension containing the omeprazole is coated at a product temperature of 35–45° C.; an atomization pressure of 1.5–3.0 bar and a pump rate of 2–50 ml/minute, starting with a slow rate of pumping to avoid agglomeration and increasing the rate of pumping consistent with the avoidance of the formation of agglomerates.

After coating is complete the pellets are dried at a temperature of 50° C. until the loss on drying is less than 2.5 wt % The pellets are then screened through a #14 mesh screen and coated with the following enteric coating formulation:

| | |
|---|---|
| hydroxypropylmethylcellulose phthalate, NF | 258.1 g |
| cetyl alcohol, NF | 12.9 g |
| talc, USP | 129.0 g |
| isopropyl alcohol, USP* | 1663.0 g |
| acetone, NF* | 1663.0 g |

*evaporates during processing

The hydroxypropylmethylcellulose phthalate and the cetyl alcohol are mixed with the isopropyl alcohol and the acetone with agitation until all of the materials are dissolved. The talc is dispersed with agitation in this solution. One kilogram of the active pellets are placed in a fluidized bed coater and all of the enteric coating mixture is applied using the coating conditions that were used to form the active pellets. The enteric coated pellets are then placed into No. "2", hard gelatin capsules containing pellets which are equivalent to 20 mg of omeprazole.

The capsules were evaluated for stability as follows:

Dissolution stability:

After acid treatment for 2 hours in 500 ml of 0.1N HCl solution at 37° C., the test samples were tested according to the USP XXII dissolution test (type 1, basket) at 100 rpm, at 370 in phosphate buffer medium, USP XXII, at pH 6.8 to determine the percent of the drug dissolved versus time. The following results were obtained:

| | Percent Dissolved | | | |
|---|---|---|---|---|
| Time (min) | initial | 40° C./ 75% RH/1 mo | 40° C./ 75% RH/2 mo | 40° C./ 75% RH/3 mo |
| 10 | 87 | 76 | 95 | 93 |
| 20 | 90 | 88 | 96 | 95 |
| 30 | 90 | 86 | 95 | 94 |
| 60 | 86 | 81 | 91 | 89 |

Chemical and Acid Resistance Stability:

The acid resistance study was conducted by using the USP XXII dissolution test (type 1, basket), 100 rpm, 37° C., in a aqueous solution of hydrochloric acid at pH 1.0. The following results were obtained:

|  | initial | 40° C./ 75% RH/1 mo | 40° C./ 75% RH/2 mo | 40° C./ 75% RH/3 mo |
| --- | --- | --- | --- | --- |
| potency (% of LC) | 101% | 101% | 100% | 100% |
| acid resistance (% of LC) | 97% | 100% | 100% | 99% |

A biostudy was carried out to compare the product of Example 1 with Prilosec brand of omeprazole (Ref. Mean) in humans. The following results were obtained in fasting humans:

| Example 1 Mean | % CV | Ref. Mean | % CV | Geometric ratio | 90% Confid. low. lim | Interv. upp. lim |
| --- | --- | --- | --- | --- | --- | --- |
| Cmax 134.50 | 61.46 | 133.46 | 60.11 | 0.964 | 72.47% | 128.19% |
| AUC 0~t 224.38 | 68.94 | 214.61 | 66.24 | 1.040 | 96.08% | 112.63% |
| AUC 0~8 230.87 | 65.78 | 220.54 | 64.76 | 1.052 | 97.42% | 113.62% |
| Tmax 2.33 | 39.90 | 1.92 | 44.93 | 1.232 | | |

All of the components which are used in the present invention are used in amounts which are effective for the intended purpose for which the component is employed.

While certain preferred and alternative embodiments of the invention have been set forth for purposes of disclosing the invention, modifications to the disclosed embodiments may occur to those who are skilled in the art. Accordingly, the appended claims are intended to cover all embodiments of the invention and modifications thereof which do not depart from the spirit and scope of the invention.

What is claimed is:

1. A pharmaceutical capsule for oral administration of omeprazole that consists essentially of a capsule and more than one pellet wherein the pellet consists of:
   (a) an inert core;
   (b) a drug layer surrounding the inert core consisting of 20–70 wt % of omeprazole, 0.1–5 wt % of a surface active agent, 20–70 wt % of a filler, 1–20 wt % of a pharmaceutically acceptable alkaline agent and 0.1–5 wt % of a binder; and
   (c) a coating layer surrounding the drug layer that consists essentially of an enteric coating agent and an inert processing aid wherein the coating layer is applied directly to the omeprazole containing drug layer without a separating layer between the omeprazole containing drug layer and the coating layer.

2. The pharmaceutical capsule as defined in claim 1 wherein the enteric coating agent comprises 90 to 20 wt % of the coating layer and the inert processing aid comprises 10 to 80 wt % of the coating layer.

3. The pharmaceutical capsule as defined in claim 2 wherein the omeprazole comprises 40–50 wt % of the drug layer; the surface active agent comprises 0.25 to 2.5 wt % of the drug layer; the filler comprises 40 to 50 wt % of the drug layer; the alkaline agent comprises 1 to 10 wt % of the drug layer; the binder comprises 0.25 to 3 wt % of the drug layer; the enteric coating agent comprises 70 to 50 wt % of the coating layer; and the inert processing aid comprises 30 to 50 wt % of the coating layer.

4. The pharmaceutical capsule as defined in claim 1 wherein the enteric coating agent is selected from the group consisting of cellulose acetate phthalate, hydroxypropyl methylcellulose phthalate, polyvinyl acetate phthalate, carboxymethylethylcellulose, co-polymerized methacrylic acid/methacrylic acid methyl esters.

5. The pharmaceutical capsule as defined in claim 1 wherein the alkaline agent is selected from the group consisting of the sodium, potassium, calcium, magnesium and aluminum salts of phosphoric acid, carbonic acid and citric acid.

6. The pharmaceutical capsule as defined in claim 1 wherein the alkaline agent is selected from the group consisting of aluminum hydroxides, calcium hydroxides, magnesium hydroxides and magnesium oxide.

7. The pharmaceutical capsule as defined in claim 1 wherein the surface active agent is sodium lauryl sulfate.

8. The pharmaceutical capsule as defined in claim 1 wherein the alkaline agent is disodium phosphate.

9. The pharmaceutical capsule as defined in claim 1 wherein the inert core is a non-pareil sugar seed.

10. The pharmaceutical capsule as defined in claim 1 wherein the omeprazole is micronized.

11. The pharmaceutical capsule as defined in claim 1 wherein the inert processing aid is selected from the group consisting of talc, silicon dioxide and magnesium stearate.

12. The stable pharmaceutical composition as defined in claim 1 wherein the binder is a water soluble polymer selected from the group consisting of polyvinyl alcohol, polyvinylpyrrolidone, methylcellulose, hydroxypropyl cellulose, and hydroxymethyl cellulose.

13. The stable pharmaceutical composition as defined in claim 1 wherein the filler is selected from the group consisting of lactose, dextrose, sucrose, maltose and microcrystalline cellulose.

14. A pharmaceutical capsule for oral administration of omeprazole that consists essentially of a capsule and more than one pellet wherein the pellet consists of:
   (a) an inert core;
   (b) a drug layer surrounding the inert core consisting of 20–70 wt % of omeprazole, 0.1–5 wt % of a surface active agent, 20–70 wt % of lactose, 1–20 wt % of a pharmaceutically acceptable alkaline agent and 0.1–5 wt % of povidone; and
   (c) a coating layer surrounding the drug layer that consists essentially of an enteric coating agent and an inert processing aid wherein the coating layer is applied directly to the omeprazole containing drug layer without a separating layer between the omeprazole containing drug layer and the coating layer.

* * * * *